(12) United States Patent
Butler

(10) Patent No.: US 8,071,836 B2
(45) Date of Patent: *Dec. 6, 2011

(54) PROCESS FOR TOLUENE AND METHANE COUPLING IN A MICROREACTOR

(75) Inventor: James R. Butler, League City, TX (US)

(73) Assignee: Fina Technology, Inc., Houston, TX (US)

( * ) Notice: Subject to any disclaimer, the term of this patent is extended or adjusted under 35 U.S.C. 154(b) by 427 days.

This patent is subject to a terminal disclaimer.

(21) Appl. No.: 12/047,930

(22) Filed: Mar. 13, 2008

(65) Prior Publication Data

US 2009/0247801 A1 Oct. 1, 2009

(51) Int. Cl.
*C07C 2/64* (2006.01)
*C07C 5/09* (2006.01)

(52) U.S. Cl. .................. 585/943; 585/452; 585/921

(58) Field of Classification Search ............... 585/452, 585/921, 943
See application file for complete search history.

(56) References Cited

U.S. PATENT DOCUMENTS

| | | | |
|---|---|---|---|
| 4,950,827 A | 8/1990 | Erekson et al. | |
| 4,950,836 A | 8/1990 | Kimble et al. | |
| 4,956,327 A * | 9/1990 | Erekson et al. | 502/216 |
| 4,982,038 A | 1/1991 | Kimble et al. | |
| 5,321,188 A * | 6/1994 | Fornasari et al. | 585/500 |
| 6,488,838 B1 | 12/2002 | Tonkovich et al. | |
| 6,960,235 B2 | 11/2005 | Morse et al. | |
| 6,984,363 B2 | 1/2006 | Tonkovich et al. | |
| 6,989,134 B2 | 1/2006 | Tonkovich et al. | |
| 7,077,643 B2 | 7/2006 | Halladay et al. | |
| 7,220,699 B2 | 5/2007 | Chellappa | |
| 2004/0034266 A1 | 2/2004 | Brophy et al. | |
| 2008/0289946 A1 | 11/2008 | Schult et al. | |
| 2008/0293983 A1 | 11/2008 | Schult et al. | |
| 2008/0293986 A1 | 11/2008 | Schult et al. | |

FOREIGN PATENT DOCUMENTS

WO  WO 03/106386  * 12/2003

OTHER PUBLICATIONS

"Falling Film Micro Reactor", Microinnova Engineering GmbH, pp. 58-59.
"Micro Bubble Column", Microinnova Engineering GmbH, pp. 60-61.
"Gas Phase Micro Reactor", Microinnova Engineering GmbH, pp. 62-63.
"Gas Phase Micro Reactor with Mixer and Internal Heating/Cooling", Microinnova Engineering GmbH, pp. 64-65.
"Catalyst Micro Burner Reactor", Microinnova Engineering GmbH, pp. 66-67.
"Catalyst Testing Micro Reactor", Microinnova Engineering GmbH, pp. 68-69.
"Counter-Flow Micro Heat Exchanger", Microinnova Engineering GmbH, pp. 70-71.
"Tube Heat Transfer Micro Device", Microinnova Engineering GmbH, pp. 72-73.
"Modular Microreaction Technology", Ehrfeld Mikrotechnik BTS GmbH, pp. 1-25 (2006).

* cited by examiner

*Primary Examiner* — Thuan D Dang

(57) ABSTRACT

A process for making ethylbenzene and/or styrene by reacting toluene with methane in one or more microreactors is disclosed. In one embodiment a method of revamping an existing styrene production facility by adding one or more microreactors capable of reacting toluene with methane to produce a product stream comprising ethylbenzene and/or styrene is disclosed.

11 Claims, 4 Drawing Sheets

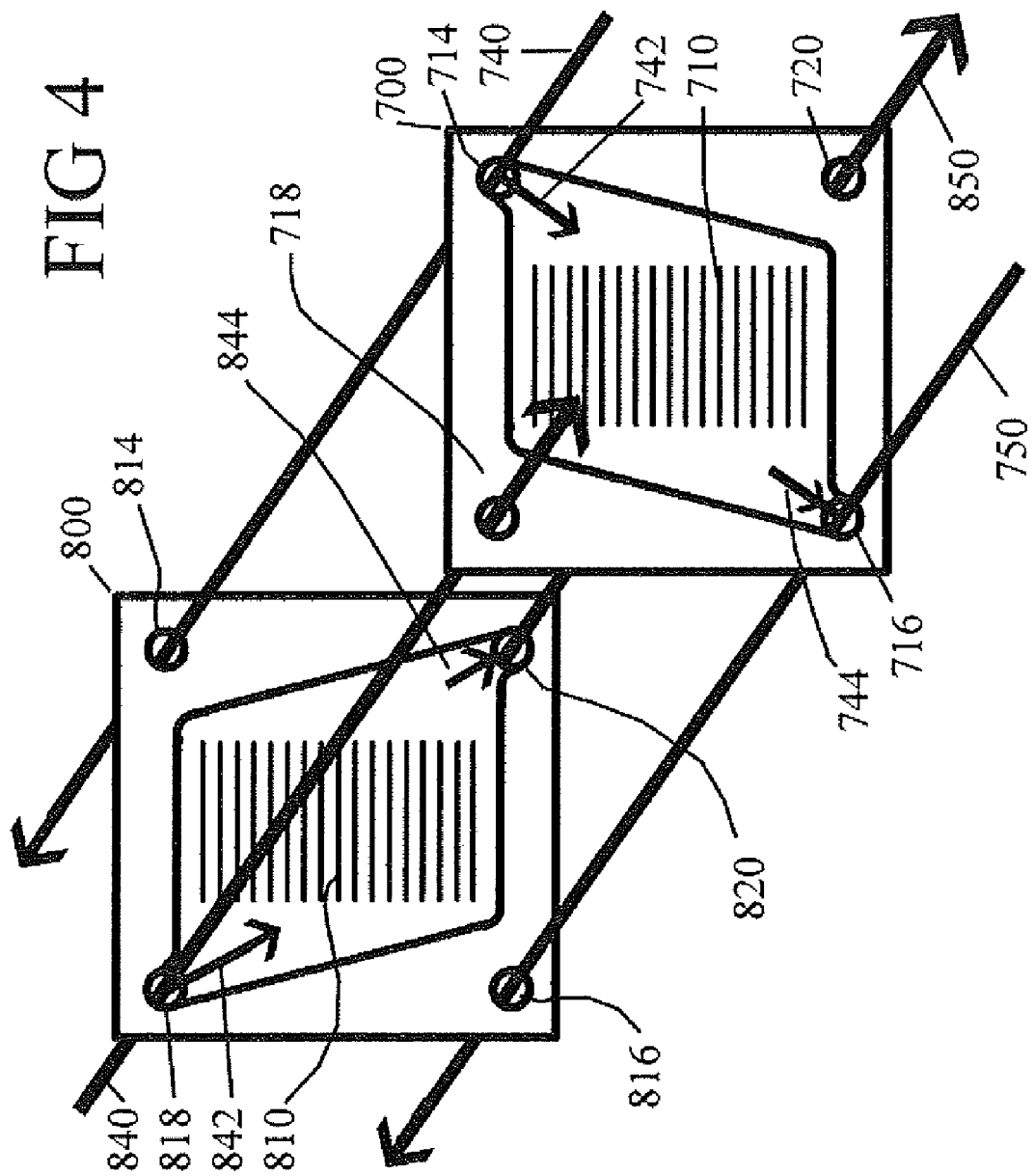

– 1 –
PROCESS FOR TOLUENE AND METHANE COUPLING IN A MICROREACTOR

BACKGROUND OF THE INVENTION

1. Field of the Invention

This invention relates generally to a process for the production of ethylbenzene and styrene.

2. Description of the Related Art

Styrene is an important monomer used in the manufacture of many of todays plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and a reduced polyalkylated content. When both alkylation and transalkylation processes are used, two separate reactors, each with its own catalyst, can be employed. The alkylation and transalkylation conversion processes can be carried out in the liquid phase, in the vapor phase or under conditions in which both liquid and vapor phases are present.

In the formation of ethylbenzene from alkylation reactions of ethylene and benzene, other impurities and undesirable side products may be formed in addition to the desired ethylbenzene. These undesirable products can include such compounds as xylene, cumene, n-propylbenzene and butylbenzene, as well as polyethylbenzenes, and high boiling point alkyl aromatic components, sometimes referred to as "heavies," having a boiling point at or above 185° C. As can be expected, reduction of these impurities and side products is important. This is especially true in the case of xylene, particularly the meta and para xylenes, which have boiling points that are close to that of ethylbenzene and can make product separation and purification difficult.

Ethylene is obtained predominantly from the thermal cracking of hydrocarbons, such as ethane, propane, butane or naphtha. Ethylene can also be produced and recovered from various refinery processes. Ethylene from these sources can include a variety of undesired products, including diolefins and acetylene, which can act to reduce the effectiveness of alkylation catalysts and can be costly to separate from the ethylene. Separation methods can include, for example, extractive distillation and selective hydrogenation of the acetylene back to ethylene. Thermal cracking and separation technologies for the production of relatively pure ethylene can account for a significant portion of the total ethylbenzene production costs.

Benzene is obtained predominantly from the hydrodealkylation of toluene which involves heating a mixture of toluene with excess hydrogen to elevated temperatures (500° C. to 600° C.) in the presence of a catalyst. Under these conditions, toluene can undergo dealkylation according to the chemical equation: $C_6H_5CH_3 + H_2 \rightarrow C_6H_6 + CH_4$ This reaction requires energy input and as can be seen from the above equation, produces methane as a byproduct, which is typically separated and used as fuel within the process.

In view of the above, it would be desirable to have a process of producing ethylbenzene, and styrene, which does not rely on thermal crackers and expensive separation technologies as a source of ethylene. It would also be desirable if the process was not dependent upon ethylene from refinery streams containing impurities which can lower the effectiveness and can contaminate the alkylation catalyst. It would further be desirable to avoid the process of converting toluene to benzene with its inherent expense and loss of a carbon atom to methane.

SUMMARY

One embodiment of the present invention is a process for making ethylbenzene which involves reacting toluene and methane in one or more microreactors to form a first product stream comprising ethylbenzene and/or styrene. The first product stream may also have one or more of benzene, toluene, methane, or styrene present. The process may comprise at least one separation process for at least partial separation of the components of the first product stream.

Methane may be separated from the first product stream which may be recycled back to the microreactors or may be utilized as fuel within the process. Toluene may also be separated from the first product stream and recycled to the microreactors. At least a portion of the components of the first product stream can be further processed in a styrene production process. The reactors can include a reaction zone and can be capable of dissipating heat to maintain the reaction zone within a desired temperature range for reacting toluene and methane to form ethylbenzene and/or styrene.

A further embodiment of the invention is a method of revamping an existing styrene production facility by adding one or more microreactors capable of reacting toluene with methane to produce a new product stream containing ethylbenzene. The new product stream containing ethylbenzene may then be sent to the existing styrene production facility for further processing to form styrene. The existing styrene production facility can include separation apparatus to remove at least a portion of any benzene from the new product stream, an alkylation reactor to form ethylbenzene by reacting the benzene with ethylene, and a dehydrogenation reactor to form styrene by dehydrogenating ethylbenzene.

Yet another embodiment of the present invention is a process for making ethylbenzene which includes reacting toluene and methane in one or more microreactors to form a first product stream comprising one or more of ethylbenzene, styrene, benzene, toluene and methane. The first product stream is sent to a separation zone where at least a portion of any methane and toluene are removed for recycle to the one or more microreactors. At least a portion of the benzene is removed from the first product stream and at least a portion of the benzene removed is reacted with ethylene in an alkylation reactor to form ethylbenzene. The ethylbenzene is dehydrogenated in one or more dehydrogenation reactors to form styrene.

The one or more microreactors may have one or more reaction zones and be capable of dissipating heat to maintain one or more of the reaction zones within a desired temperature range to promote reacting toluene and methane to form ethylbenzene and/or styrene. The one or more microreactors can comprise a plurality of microstructured panels creating a reaction zone comprising a plurality of microchannels. A portion of the microstructured panels can create reaction zones comprising a plurality of reaction zone microchannels and a portion of the microstructured panels can create a plurality of cooling microchannels for the flow of a cooling medium capable of dissipating heat to maintain the reaction zones within a desired temperature range for reacting toluene and methane to form ethylbenzene. The plurality of microstructured panels can be arranged in an alternating manner so the reaction zone microchannels and the cooling microchannels are capable of dissipating heat to maintain the reaction zones within a desired temperature range for reacting toluene and methane to form ethylbenzene.

BRIEF DESCRIPTION OF THE DRAWINGS

FIG. 4 is an illustrated example of two microstructured panels, each having microchannels, one for reactants and the other for a cooling medium.

DETAILED DESCRIPTION

Figure 1:
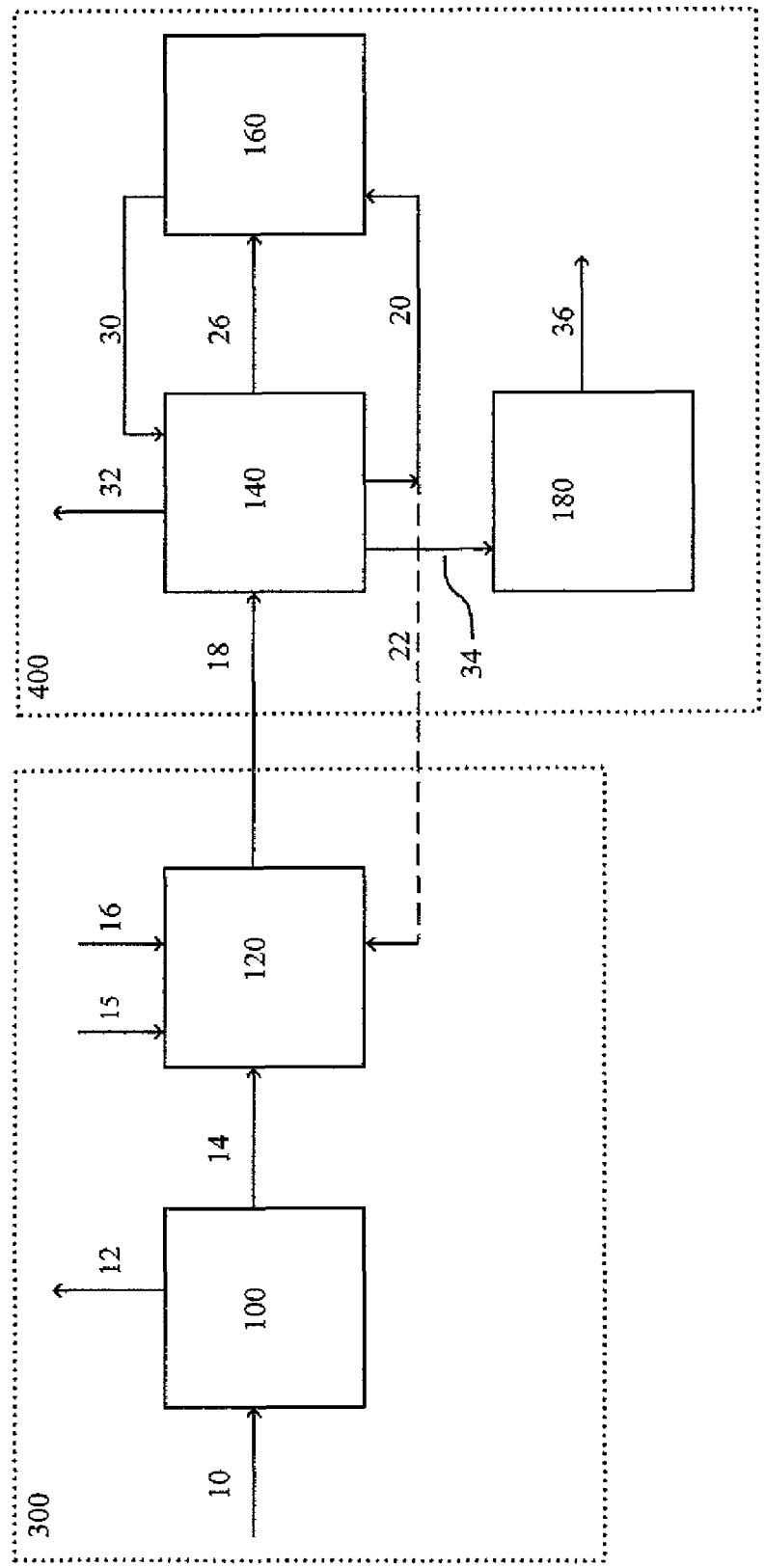
FIG. 1 is a schematic block diagram illustrating a process for making ethylbenzene and styrene.

Referring first to FIG. 1, there is illustrated a schematic block diagram of a typical alkylation/transalkylation process carried out in accordance with the prior art. A feed stream of toluene is supplied via line 10 to reactive zone 100 which produces product streams of methane via line 12 and benzene via line 14. The benzene via line 14 along with ethylene via line 16 are supplied to an alkylation reactive zone 120 which produces ethylbenzene and other products which are sent via line 18 to a separation zone 140. The separation zone 140 can remove benzene via line 20 and send it to a transalkylation reaction zone 160. The benzene can also be partially recycled via line 22 to the alkylation reactive zone 120. The separation zone 140 can also remove polyethylbenzenes via line 26 which are sent to the transalkylation reaction zone 160 to produce a product with increased ethylbenzene content that can be sent via line 30 to the separation zone 140. Other byproducts can be removed from the separation zone 140 as shown by line 32, this can include methane and other hydrocarbons that can be recycled within the process, used as fuel gas, flared or otherwise disposed of. Ethylbenzene can be removed from the separation zone 140 via line 34 and sent to a dehydrogenation zone 180 to produce styrene product that can be removed via line 36.

The front end of the process 300, designated by the dashed line, includes the initial toluene to benzene reactive zone 110 and the alkylation reactive zone 120. It can be seen that the input streams to the front end 300 include toluene via line 10, ethylene via line 16 and optionally oxygen via line 15. There can also be input streams of benzene from alternate sources other than from a toluene reaction, although they are not shown in this embodiment. The output streams include the methane via line 12 which is produced during the conversion of toluene to benzene in reactive zone 110 and the product stream containing ethylbenzene via line 18 that is sent to the back end of the process 400. The back end 400 includes the separation zone 140, the transalkylation reaction zone 160 and the dehydrogenation zone 180.

Figure 2:
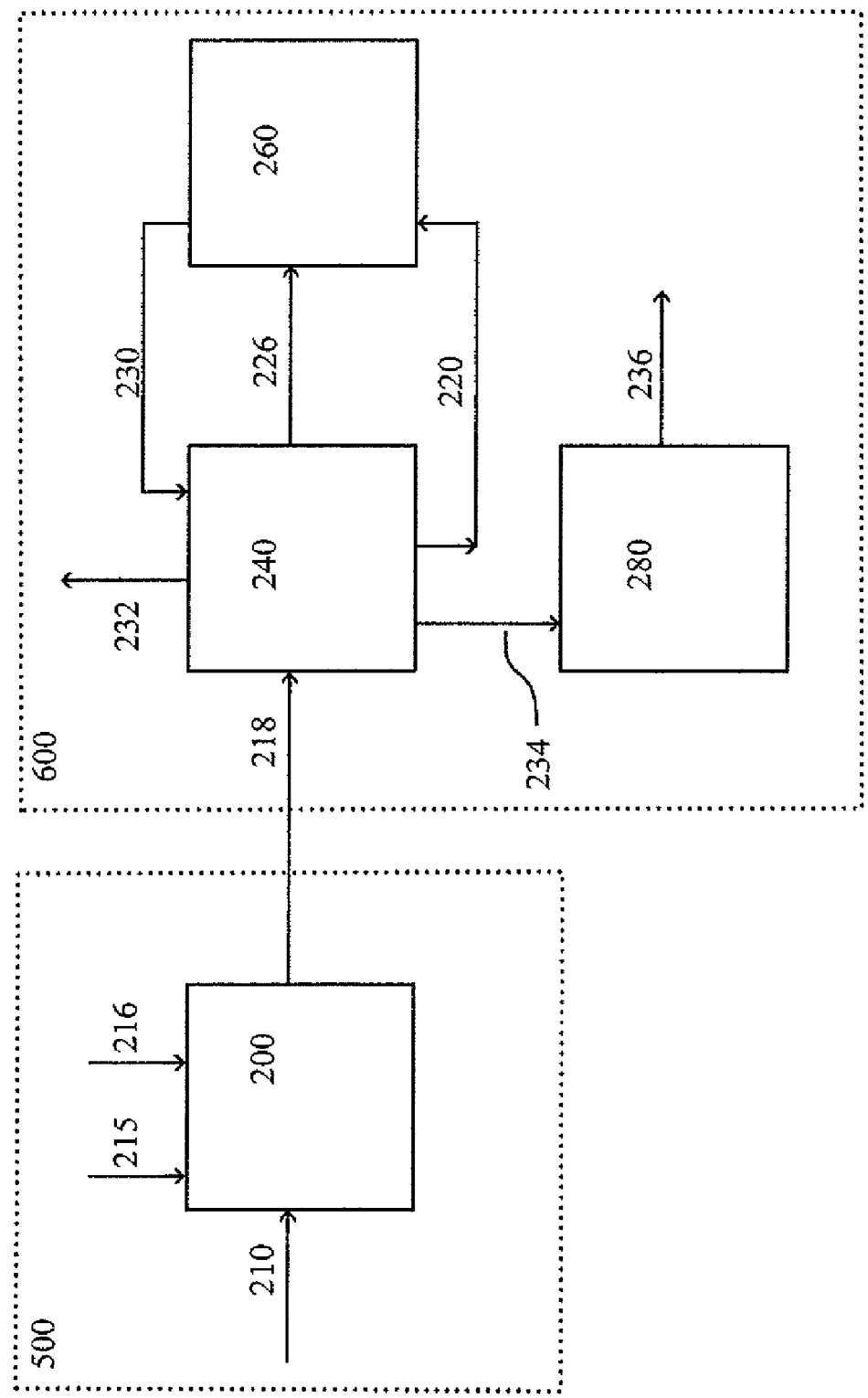
FIG. 2 is a schematic block diagram illustrating a process for making ethylbenzene and styrene according to an embodiment of the present invention.

Turning now to FIG. 2, there is illustrated a schematic block diagram of one embodiment of the present invention. Feed streams of toluene supplied via line 210 and methane supplied via line 216 are supplied to one or more microreactors 200 which produces ethylbenzene along with other products, which can include styrene. In some embodiments an input stream of oxygen 215 may be supplied to the microreactors 200. The output from the microreactor 200 includes a product containing ethylbenzene which is supplied via line 218 to a separation zone 240. The separation zone 240 can separate benzene that may be present via line 220 which can be sent to an alkylation reaction zone 260. The alkylation reaction zone 260 can include a transalkylation zone. The separation zone 240 can also remove heavy molecules that may be present via line 226. The alkylation reaction zone 260 can produce a product with increased ethylbenzene content that can be sent via line 230 to the separation zone 240. Other byproducts can be removed from the separation zone 240 as shown by line 232, this can include methane and other hydrocarbons that can be recycled within the process, used as fuel gas, flared or otherwise disposed of. Ethylbenzene can be removed from the separation zone 240 via line 234 and sent to a dehydrogenation zone 280 to produce styrene product that can be removed via line 236. Any styrene that is produced from the reactive zone 200 can be separated in the separation zone 240 and sent to the dehydrogenation zone 280 via line 234 along with the ethylbenzene product stream, or can be separated as its own product stream, (not shown), bypassing the dehydrogenation zone 280 and added to the styrene product in line 236.

The front end of the process 500 includes the one or more microreactors 200 which can be in series or parallel arrangements. The input streams to the front end 500 are toluene via line 210 and methane via line 216 and optionally oxygen via line 215. The output stream is the product containing ethylbenzene via line 218 that is sent to the back end of the process 600. The back end 600 includes the separation zone 240, the alkylation reaction zone 260 and the dehydrogenation zone 280.

A comparison of the front end 300 of the prior art shown in FIG. 1 against the front end 500 of the embodiment of the invention shown in FIG. 2 can illustrate some of the features of the present invention. The front end 500 of the embodiment of the invention shown in FIG. 2 has a single microreactor zone 200 rather than the two reactive zones contained within the front end 300 shown in FIG. 1, the reactive zone 100 and the alkylation reactive zone 120. The reduction of one reactive zone can have a potential cost savings and can simplify the operational considerations of the process.

Both front ends have an input stream of toluene, shown as lines 10 and 210. The prior art of FIG. 1 has an input stream of ethylene 16 and a byproduct stream of methane 12. The embodiment of the invention shown in FIG. 2 has an input stream of methane 216. The feed stream of ethylene 16 is replaced by the feed stream of methane 216, which is typically a lower value commodity, and should result in a cost savings. Rather than generating methane as a byproduct 12 which would have to be separated, handled and disposed of, the present invention utilizes methane as a feedstock 216 to the microreactor 200.

A comparison of the back end 400 of the prior art shown in FIG. 1 with the back end 600 of the embodiment of the invention shown in FIG. 2 can further illustrate the features of the present invention. It can be seen that the back end 400 of the prior art shown in FIG. 1 is essentially the same as the back end 600 of the embodiment of the invention shown in FIG. 2. They each contain a separation zone, an alkylation reaction zone and a dehydrogenation zone and are interconnected in the same or essentially the same manner. This aspect of the present invention can enable the front end of a facility to be modified in a manner consistent with the invention, while the back end remains essentially unchanged. A revamp of an existing ethylbenzene or styrene production facility can be accomplished by installing a new front end or modifying an existing front end in a manner consistent with the invention and delivering the product of the altered front end to the existing back end of the facility to complete the process in essentially the same manner as before. The ability to revamp an existing facility and convert from a toluene/ethylene feedstock to a toluene/methane feedstock by the modification of the front end of the facility while retaining the existing back end can have significant economic advantages.

The microreactor 200 of the present invention can comprise one or more single or multi-stage microreactors. In one embodiment the microreactor 200 can have a plurality of microreactors connected in series (series-connected microreactors). Additionally and in the alternative, the microreactors may be arranged in a parallel fashion. The microreactor 200 can be operated at temperature and pressure conditions to enable the reaction of toluene and methane to form ethylbenzene, and at a feed rate to provide a space velocity enhancing ethylbenzene production while retarding the production of xylene or other undesirable products. The reactants, toluene and methane, can be added to the plurality of series-connected microreactors in a manner to enhance ethylbenzene production while retarding the production of undesirable products. For example toluene and/or methane can be added to any of the plurality of series-connected microreactors as needed to enhance ethylbenzene production.

The microreactor 200 can be operated in the vapor phase. One embodiment can be operated in the vapor phase within a pressure range of 4 psia to 1000 psia. Another embodiment can be operated in the vapor phase within a pressure range of atmospheric to 500 psia.

The feed streams of methane and toluene can be supplied to the microreactor 200 in ratios of from 2 to 50 moles methane to toluene. In one embodiment the ratios can range from 5 to 30 moles methane to toluene.

In one embodiment of the invention oxygen is added to the microreactor 200 in amounts that can facilitate the conversion of toluene and methane to ethylbenzene and styrene. The oxygen content can range from 1% to 50% by volume relative to the methane content. In one embodiment the oxygen content can range from 2% to 30% by volume relative to the methane content.

In one embodiment the microreactor 200 of the present invention can comprise multiple microreactors and oxygen can be added to the plurality of series-connected microreactors in a manner to enhance ethylbenzene and/or styrene production while retarding the production of undesirable products. Oxygen can be added incrementally to each of the plurality of series-connected microreactors as needed to enhance ethylbenzene and/or styrene production, to limit the exotherm from each of the microreactors, to maintain the oxygen content within a certain range throughout the plurality of microreactors or to customize the oxygen content throughout the plurality of microreactors. In one embodiment there is the ability to have an increased or reduced oxygen content as the reaction progresses and the ethylbenzene and/or styrene fraction increases while the toluene and methane fractions decrease. There can be multiple series-connected microreactors which are arranged in a parallel manner.

The oxygen can react with a portion of the methane and result in a highly exothermic reaction. The heat generated by the exothermic reaction can be regulated to some extent by the use of microreactors which can have a large surface area to reactant contact area ratio. The small contact area for the reactants can result in a short residence time for the reaction, which in some embodiments can be as short as less than a second. The shortened residence time and large surface area to reactant contact area ratio can facilitate heat dissipation from the microreactor. These factors, along with the ability for incremental oxygen addition to the plurality of series-connected microreactors, can be used to control the reaction temperatures within a range to facilitate the production of ethylbenzene and/or styrene and reduce the production of undesired components. Microreactors with integrated cooling can also be used, thus a short residence time reactor with an integrated heat exchanger can be used.

When a plurality of series-connected microreactors are utilized, counter-flow micro heat exchangers can be used to dissipate heat and provide temperature control for the reaction. In one embodiment a plurality of series-connected microreactors are utilized and one or more counter-flow micro heat exchangers are located between two or more of the microreactors used to dissipate heat and provide temperature control for the individual microreactors and the overall reaction. One temperature range to facilitate the production of ethylbenzene and/or styrene is from 550° C. to 1000° C. Another temperature range to facilitate the production of ethylbenzene and/or styrene is from 600° C. to 800° C. The heat generated by the exothermic reaction can be removed and recovered to be utilized within the process.

In one embodiment the microreactor zone 200 of the present invention can comprise one or more single or multi-stage microreactors which can contain one or more single or multi-stage catalyst sites. The catalyst that can be used in the microreactor 200 can include any catalyst that can couple toluene and methane to make ethylbenzene and/or styrene and are not limited to any particular type. It is believed that the oxidation reaction of toluene and methane can be accelerated by base catalysis. In one non-limiting example the catalyst can comprise one or more metal oxides. In one non-limiting example the catalyst can contain a metal oxide which is supported on an appropriate substrate. It is believed that with a metal oxide catalyst the oxygen/oxide sites can function as the active reaction centers which can remove hydrogen atoms from the methane to form methyl radicals and from the toluene to form benzyl radicals. The C8 hydrocarbons can be formed as a result of cross-coupling between the resulting methyl and benzyl radicals. The catalysts may contain different combinations of alkali, alkaline earth, rare earth, and/or transition metal oxides. In another non-limiting example the catalyst can comprise a modified basic zeolite. In yet another non-limiting example the catalyst can be a base zeolite, such as an X, Y, mordenite, ZSM, silicalite or AlPO4-5 that can be modified with molybdenum, sodium or other basic ions. The zeolite catalyst may or may not contain one of more metal oxides.

A catalyst can be introduced into one or more parts of the process. In one embodiment the microchannels of the microreactor can have a catalyst deposited or impregnated on or within them. The catalyst can also be affixed to an article, such as a rod, that can be contained or inserted into the microreactor in a manner which can contact the catalyst with the reactant streams. Alternatively, a process for wash coating a carrier with catalyst can be used where the carrier is capable of contacting the reactants within one or more of the microreactors. The catalyst can be contacted with the reactants at one or more points of the plurality of series-connected microreactors. The catalyst can alternately be contacted with the reactants at one or more points between the plurality of series-connected microreactors, such as for example at a location between two microreactors in conjunction with a counter-flow micro heat exchanger.

Figure 3:
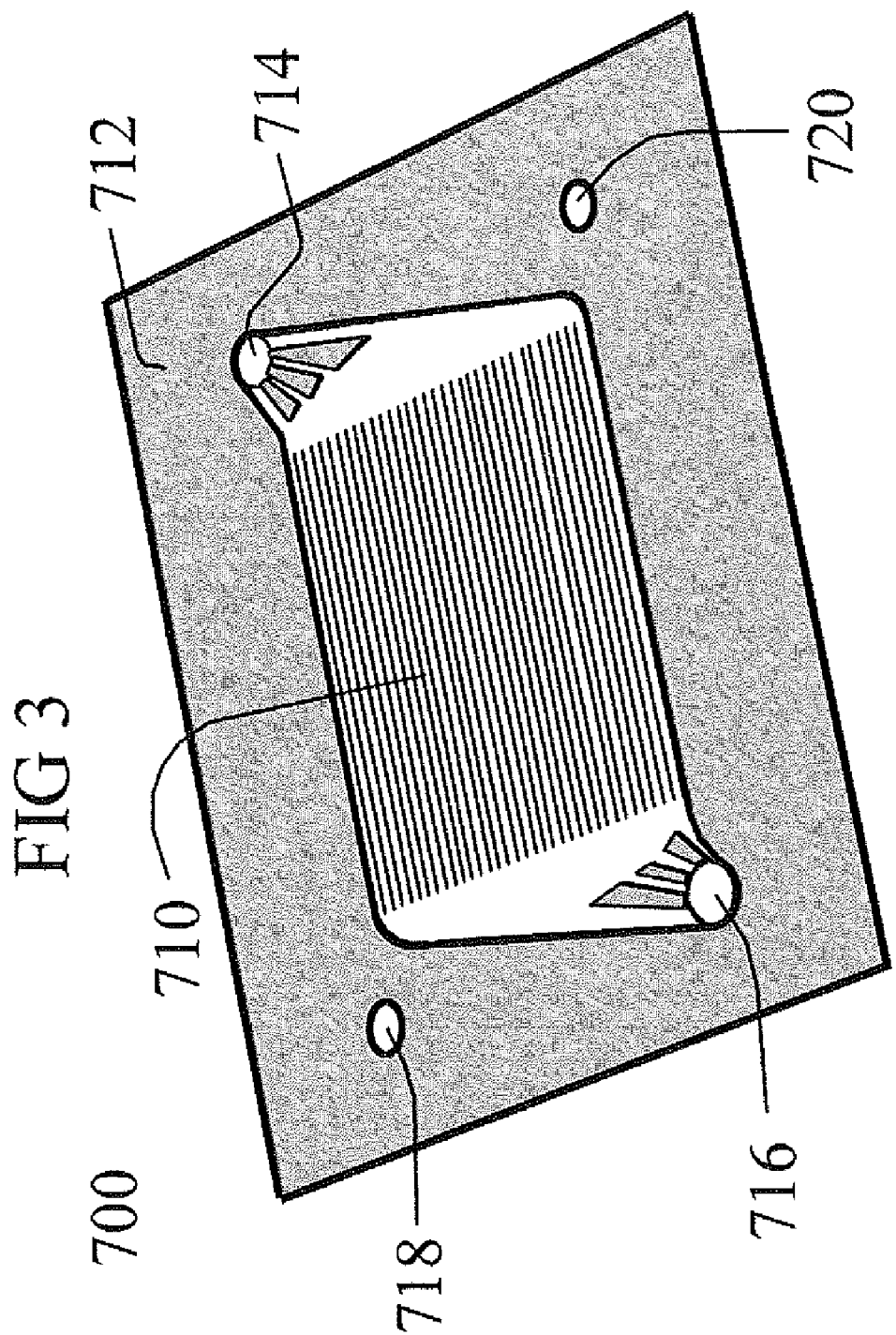
FIG. 3 is an illustrated example of a microstructured panel.

Referring now to FIG. 3, the microreactor can comprise a number of microstructured panels 700 that can have recesses or channels of small depth that serve as flow channels or microchannels 710. These types of microreactors can be similar to typical plate-and-frame type heat exchangers known in the art, but of much smaller size. In one embodiment the microreactor panels 700 can range from about 30 to 50 mm in length and from about 30 to 50 mm in height. The microreactor panels 700 can be constructed by micro-machining or etching a panel made of metals, silicon, glass or ceramic materials, which can be referred to as a substrate material. Microchannels 710 can be etched or otherwise formed in a pattern on the surface 712 of the substrate panel material. In one embodiment the number of microchannels formed on the surface of the panel can range from 10 to 5000. The microchannels 710 can be in fluid communication with openings through the panels which can serve as inlet 714 and outlet 716 passages between the microreactors and/or microchannels so that the reactants can enter and exit the microchannels. The panel 700 may also have pass-though holes 718, 720 that can allow a fluid or gas to pass through the panel 700 without being in contact with the panel inlet 714, outlet 716 or the microchannels 710. The pass-though holes 718, 720 in one embodiment have a diameter of from 0.5 mm to 2.0 mm. The width and depth of the microchannels 710 in one embodiment can range from 100 µm to 300 µm while the total depth of the panel 700 can range from 400 µm to 600 µm. In another embodiment the width and depth of the microchannels can range from 100 µm to 500 µm while the total depth of the panel 700 can range from 700 µm to 1 mm. In yet another embodiment the width and depth of the microchannel can range from 300 µm to 600 µm while the total depth of the panel 700 can range from 800 µm to 1.5 mm or more. The width and depth of the microchannels do not have to be consistent or have the same dimensions of the other microchannels. While in some embodiments the width may be of a larger dimension than the depth, in other embodiments the depth may be of a larger dimension than the width. If plugging is a concern, having the depth and width of the microchannels be of similar dimension to create a more uniform cross sectional flow area of the microchannel may be desired.

In yet another embodiment the microreactor panels 700 can range from about 300 mm to 900 mm in length and from about 300 mm to 900 mm in height. The width of the microchannel 710 of these larger panels can be as large as 5 mm while the depth of the microchannel 710 would still be limited to a dimension less than that of the substrate panel material. The size of the panels and dimensions of the microchannels can vary greatly while still being within the scope of the present invention.

Referring now to FIG. 4, in one embodiment a reactant inlet stream 740 supplies an inlet stream 742 to the microchannels 710 of panel 700. The reactants can flow through the microchannels 710 and exit panel 700 in outlet stream 744 to combine in the product stream 750. The reactant inlet stream 740 can pass through the opening 814 of panel 800 without being in contact with the fluids flowing through the microchannels 810 of panel 800. The product stream 750 can likewise pass through the opening 816 of panel 800 without being in contact with the fluids flowing through the microchannels 810 of panel 800. A cooling medium stream 840 supplies an inlet stream 842 to the microchannels 810 of panel 800. The cooling medium can flow through the microchannels 810 and exit panel 800 in outlet stream 844 to combine in the cooling medium exit stream 850. The cooling medium inlet stream 840 can pass through the opening 718 of panel 700 without being in contact with the reactants flowing through the microchannels 710 of panel 700. The cooling medium outlet stream 850 can pass through the opening 720 of panel 700 without being in contact with the reactants flowing through the microchannels 710 of panel 700. The microreactor would comprise a plurality of panels that are pressed together in a manner to enable the reactants and cooling medium stream to be contained within their respective flow paths and not in communication with each other. A gasket material, a solder material, or a brazing material can be used to provide a seal between the panels.

Multiple microreactors can be utilized in a facility. In one embodiment the number of panels can range from 2 to 100. In an alternate embodiment the number of panels can range from 100 to 3000. In a commercial scale petrochemical plant the number of panels that can be used can reach hundreds or thousands, with up to a million channels or more per reactor.

As can be seen in FIG. 4, in one embodiment the microreactor can comprise alternating panels, to provide reactant flow through the microchannels of every other panel, while a different fluid, such as a cooling medium, can be flowing through the alternate panels. The different fluid, such as a cooling medium, can be flowing through the alternate panels in a counter-flow or co-current flow in relation to the reactant flow. Dissipation of the exotherm is through the panel material that make up the microchannel walls containing the reactants and into the cooling medium that is flowing through the microchannels created by the adjacent panels. This enables a rapid heat dissipation and the ability to control the reaction temperature within the microchannel in a manner that conventional reactors can not achieve.

The substrate material used for panel construction can act as a catalyst, or the microchannels may be coated with a catalyst layer, for example by using a wash coating or thin-film deposition of a catalyst material within or adjacent to the microchannels. A catalyst material can also be placed within a recess of the panel material that is in fluid contact with the reactants flowing through the microchannels, such as just before the reactants enter the microchannels.

Other types of microreactors can be used within the scope of the present invention. The description of multiple panel microreactors is not meant to be a limiting example of the microreactor. Another microreactor that can be used is a Falling Film microreactor which utilizes a multitude of thin falling films flowing through a multi-channel reactor.

Microreactors can be provided by sources such as Atotech located in Berlin, Germany; Velocys located in Plain City, Ohio, USA; Microinnova located in Graz, Austria; and Ehrfeld Mikrotechnik BTS GmbH located in Wendelsheim, Germany. Further, other types or brands of microreactors can be used in conjunction with the present invention.

The foregoing description of certain embodiments of the present invention have been presented for purposes of illustration and description. It is not intended to be exhaustive or limit the invention to the precise form disclosed, and other and further embodiments of the invention may be devised without departing from the basic scope thereof. It is intended that the scope of the invention be defined by the accompanying claims and their equivalents.

The invention claimed is:

1. A process for making ethylbenzene and styrene comprising:
    reacting toluene and methane in one or more microreactors to form a first product stream comprising ethylbenzene and styrene;
    wherein the one or more microreactors comprises a reaction zone and wherein the one or more microreactors are capable of dissipating heat to maintain the reaction zone within a desired temperature range for reacting toluene and methane to form ethylbenzene and styrene;

wherein the reaction zone comprises one or more catalyst sites comprising a catalyst selected from the group consisting of X zeolite, Y zeolite, mordenite, silicalite, and combinations thereof; wherein the catalyst is modified with molybdenum, sodium or other basic ions.

2. The process of claim 1, wherein at least a portion of the components of the first product stream are further processed in a subsequent styrene production process.

3. The process of claim 2, wherein the subsequent styrene production process comprises:

reacting benzene and ethylene in one or more alkylation reactors to form ethylbenzene; and dehydrogenating ethylbenzene in one or more dehydrogenation reactors to form styrene.

4. The process of claim 1, wherein the first product stream further comprises one or more of benzene, toluene, or methane.

5. The process of claim 1, wherein the process further comprises at least one separation process for at least partial separation of the components of the first product stream.

6. The process of claim 5 further comprising removing at least a portion of any methane from the first product stream to form a second product stream with reduced methane content.

7. The process of claim 5, wherein methane is removed from the first product stream and recycled as an inlet stream to the one or more microreactors.

8. The process of claim 5, wherein toluene is removed from the second product stream and recycled as an inlet stream to the one or more microreactors.

9. The process of claim 1, wherein the one or more microreactors comprise a plurality of microstructured panels, a portion of the microstructured panels creating reaction zones comprising a plurality of reaction zone microchannels and a portion of the microstructured panels creating a plurality of cooling microchannels for the flow of a cooling medium capable of dissipating heat to maintain the reaction zones within a desired temperature range for reacting toluene and methane to form ethylbenzene and styrene.

10. The process of claim 9, wherein the plurality of microstructured panels are arranged in an alternating manner so the reaction zone microchannels and the cooling microchannels are capable of dissipating heat to maintain the reaction zones within a desired temperature range for reacting toluene and methane to form ethylbenzene and styrene.

11. The process of claim 9, wherein the plurality of reaction zone microchannels and the plurality of cooling microchannels each comprise widths ranging from 100 to 500 μm.

* * * * *